United States Patent
Walsh

(10) Patent No.: US 11,083,603 B2
(45) Date of Patent: Aug. 10, 2021

(54) CONTRACTING STENT WITH BIORESORBABLE STRUTS

(71) Applicant: Cardinal Health Switzerland 515 Gmbh, Baar (CH)

(72) Inventor: Quentin Walsh, Livermore, CA (US)

(73) Assignee: Cardinal Health Switzerland 515 Gmbh, Baar (CH)

( * ) Notice: Subject to any disclaimer, the term of this patent is extended or adjusted under 35 U.S.C. 154(b) by 73 days.

(21) Appl. No.: 16/088,489

(22) PCT Filed: Mar. 29, 2016

(86) PCT No.: PCT/IB2016/000493
§ 371 (c)(1),
(2) Date: Sep. 26, 2018

(87) PCT Pub. No.: WO2017/168190
PCT Pub. Date: Oct. 5, 2017

(65) Prior Publication Data
US 2019/0091047 A1    Mar. 28, 2019

(51) Int. Cl.
*A61F 2/90*    (2013.01)
*A61F 2/915*   (2013.01)

(52) U.S. Cl.
CPC .............. *A61F 2/90* (2013.01); *A61F 2/915* (2013.01); *A61F 2002/91541* (2013.01);
(Continued)

(58) Field of Classification Search
CPC .. A61F 2/90; A61F 2/915; A61F 2002/91541; A61F 2002/91533;
(Continued)

(56) References Cited

U.S. PATENT DOCUMENTS

| 5,383,926 A | 1/1995 | Lock et al. |
| 5,405,377 A * | 4/1995 | Cragg ................ A61F 2/90 623/1.2 |

(Continued)

FOREIGN PATENT DOCUMENTS

DE    10105160 A1    8/2002

OTHER PUBLICATIONS

International Preliminary Report on Patentability and Written Opinion for Application No. PCT/IB2016/000493 dated Oct. 2, 2018, 7 pages.

(Continued)

*Primary Examiner* — Paul B Prebilic
(74) *Attorney, Agent, or Firm* — Dergosits & Noah LLP; Todd A. Noah

(57) ABSTRACT

A stent is formed from an at least partially cylindrical non-bioresorbable framework with a longitudinal zone of the stent that extends from the proximal end of the framework to the distal end and is defined by opposing longitudinal edges. A plurality of bioresorbable struts are secured to opposing longitudinal edges of the longitudinal zone. The bioresorbable struts hold the opposing longitudinal edges a first distance apart at an expanded deployed diameter to apposition the framework against a wall defining the vessel. After the stent is endothelialized, degradation of the bioresorbable struts causes the stent to contract to a reduced deployed diameter so that the opposing longitudinal edges are a second distance apart that is less than the first distance.

16 Claims, 4 Drawing Sheets

(52) U.S. Cl.
CPC ............... *A61F 2002/91575* (2013.01); *A61F 2210/0004* (2013.01); *A61F 2210/0014* (2013.01); *A61F 2220/0025* (2013.01); *A61F 2230/0006* (2013.01); *A61F 2230/0054* (2013.01); *A61F 2230/0056* (2013.01); *A61F 2230/0091* (2013.01); *A61F 2250/0031* (2013.01); *A61F 2250/0067* (2013.01)

(58) Field of Classification Search
CPC .... A61F 2002/9155; A61F 2002/91558; A61F 2210/0004; A61F 2210/0014; A61F 2230/0006; A61F 2230/0091; A61F 2250/003; A61F 2250/0031
USPC ........................................................ 623/1.22
See application file for complete search history.

(56) References Cited

U.S. PATENT DOCUMENTS

| | | | | |
|---|---|---|---|---|
| 5,954,765 A | * | 9/1999 | Ruiz | A61F 2/92 606/194 |
| 5,961,545 A | * | 10/1999 | Lentz | A61F 2/07 606/191 |
| 6,258,117 B1 | * | 7/2001 | Camrud | A61F 2/90 623/1.16 |
| 6,350,277 B1 | * | 2/2002 | Kocur | A61F 2/90 623/1.11 |
| 6,730,117 B1 | * | 5/2004 | Tseng | A61F 2/88 623/1.16 |
| 8,425,587 B2 | * | 4/2013 | Trollsas | A61L 31/148 623/1.16 |
| 2006/0064158 A1 | * | 3/2006 | Bales | A61F 2/91 623/1.22 |
| 2006/0079955 A1 | * | 4/2006 | Brown | A61F 2/88 623/1.22 |
| 2008/0215129 A1 | * | 9/2008 | Venturelli | A61F 2/91 623/1.11 |
| 2009/0306766 A1 | * | 12/2009 | McDermott | A61F 2/88 623/1.16 |
| 2013/0237929 A1 | * | 9/2013 | Hong | A61B 17/0057 604/264 |

OTHER PUBLICATIONS

International Search Report and Written Opinion for Application No. PCT/IB2016/000493, dated Oct. 21, 2016, 11 pages.

\* cited by examiner

CONTRACTING STENT WITH BIORESORBABLE STRUTS

FIELD OF THE PRESENT DISCLOSURE

This disclosure generally relates a stent for treating venous insufficiency and more particularly to a stent having an expanded deployed diameter maintained by bioresorbable elements that degrade after endothelialization, causing the stent to contract to a reduced deployed diameter and return the vessel in which it is deployed to a desired diameter.

BACKGROUND

It is known in the medical field to utilize an implantable prosthesis to support a duct or vessel in a mammalian body. One such prosthesis may include a frame-like structure. Such frame-like structures are commonly known as a "stent," "stent-graft" or "covered stent." For the purpose of discussion, these structures are referred to collectively herein as a "stent."

The stent can be utilized to support a duct or vessel in the mammalian body that suffers from an abnormal widening (e.g., an aneurysm, vessel contraction or lesion such as a stenosis or occlusion), or an abnormal narrowing (e.g., a stricture). Stents are also utilized widely in the urethra, esophagus, biliary tract, intestines, arteries, veins, as well as peripheral vessels. The stent can be delivered via a small incision on a host body. Hence, the use of stents as a minimally invasive surgical procedure has become widely accepted.

The stents can be cut from a tube or wound from a wire on a mandrel. Thereafter, the stents can be expanded in the duct or vessel of a host by a separate mechanism (e.g., balloon) or by utilization of a material that self-expands upon predetermined implantation conditions.

One common form of the stent is configured as a series of essentially identical hoops or rings connected together to form a lattice-like framework that defines a cylindrical or tubular framework. The series of rings may or may not have connecting linkages between the adjacent rings. Another common stent design may be formed by winding of an undulating member helically about a longitudinal axis to form the cylindrical or tubular framework. Both designs may utilize a biocompatible metal alloy (e.g., Nitinol or Elgiloy). The most common metal alloy utilized by these examples is Nitinol which has strong shape memory characteristics, causing the stent to self-expand when placed in the duct or vessel of a mammalian body at normal body temperature.

Attempts have been made to impart additional functionality to a stent by using materials that are bioresorbable or biodegradable. For example, U.S. Pat. No. 6,258,117 shows and describes that longitudinally adjacent portions of a stent may be connected to each other via breakable or biodegradable links or connectors. U.S. Pat. No. 6,287,332 discloses stents that are formed entirely of a bioresorbable material that completely degrades over time. Further, U.S. Patent Publication No. 2005/0222671 also discloses a stent formed from a series of ring-link segments connected by biodegradable connectors, as well as noting the rings themselves may be biodegradable. Likewise, U.S. Patent Publication No. 2006/0079955 discloses that a stent may be formed from a bioresorbable polymer or alloy. U.S. Patent Publication No. 2008/0234831 also discloses polymeric stents that may be formed from a bioresotbable material. Finally, U.S. Pat. No. 8,647,379 discloses a helically wound stent that features bioresorbable connectors between longitudinally adjacent windings.

However, none of these references recognize that selective use of a bioresorbable material may allow a stent to initially assume an expanded deployed diameter in one operational state that contracts to reduced deployed diameter in another operational state following degradation of the bioresorbable material. Accordingly, the techniques of this disclosure as described in the following materials satisfy this and other needs.

SUMMARY

The present disclosure is directed to a stent including a non-bioresorbable framework extending along a longitudinal axis having an at least partially cylindrical shape with proximal and distal ends, a longitudinal zone of the stent extending from the proximal end of the framework to the distal end, wherein the longitudinal zone is defined by opposing longitudinal edges and a plurality of bioresorbable struts, wherein each bioresorbable strut is secured to the opposing longitudinal edges of the longitudinal zone wherein the stent can assume an expanded deployed diameter in one operational state with the plurality of bioresorbable struts holding the opposing longitudinal edges a first distance apart and wherein the stent will contract to a reduced deployed diameter in another operational state upon degradation of the plurality of bioresorbable struts so that the opposing longitudinal edges are a second distance apart that is less than the first distance.

In one aspect, the non-bioresorbable framework has sufficient resiliency to cause the stent to contract to the reduced deployed diameter when the plurality of bioresorbable struts degrade. For example, the non-bioresorbable framework may be formed from a nickel titanium shape memory alloy.

In one aspect, the stent also has at least one non-bioresorbable strut that is secured to the opposing longitudinal edges of the longitudinal zone, wherein the non-bioresorbable framework and the at least one non-bioresorbable strut have sufficient resiliency to cause the stent to contract to the reduced deployed diameter when the plurality of bioresorbable struts degrade. At least one of the non-bioresorbable framework and the at least one non-bioresorbable strut or both may be formed from a nickel titanium shape memory alloy.

In one aspect, the plurality of bioresorbable struts are formed from a metal alloy.

In one aspect, the plurality of bioresorbable struts are formed from a polymer.

In one aspect, the plurality of bioresorbable struts may degrade over a time period greater than a time period required for the stent to be endothelialized. For example, the plurality of bioresorbable struts may degrade over a time period greater than approximately 30 days.

In one aspect, the framework may include a plurality of arcuate sections circumscribing a longitudinal axis from the proximal end to the distal end, the plurality of arcuate sections spaced apart along the longitudinal axis to form at least one continuous helical path about the longitudinal axis except within the longitudinal zone. At least one bioresorbable strut may be secured to ends of a same helical winding to continue the helical path through the longitudinal zone or at least one bioresorbable strut may be secured to ends of different helical windings.

In one aspect, the framework may include a plurality of hoops spaced apart along a longitudinal axis with adjacent hoops connected to each other by respective connector members, each hoop comprising a repeating pattern of generally longitudinally aligned strut members connected by loop members. At least one bioresorbable strut may be secured to ends of a same hoop to form a continuous hoop or at least one bioresorbable strut may be secured to ends of different hoops.

This disclosure also includes a method for treating a patient, which may involve providing a stent having an at least partially cylindrical non-bioresorbable framework extending along a longitudinal axis with proximal and distal ends, wherein a longitudinal zone of the stent extends from the proximal end of the framework to the distal end and is defined by opposing longitudinal edges, and a plurality of bioresorbable struts secured to opposing longitudinal edges of the longitudinal zone, positioning the stent within a vessel of the patient in an operational state having an expanded deployed diameter, so that the plurality of bioresorbable struts hold the opposing longitudinal edges a first distance apart, wherein the framework is in apposition with a wall defining the vessel. The bioresorbable struts may be allowed to degrade following endothelialization of the stent, wherein degradation of the bioresorbable struts causes the stent to contract to another operational state having a reduced deployed diameter so that the opposing longitudinal edges are a second distance apart that is less than the first distance.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which.

DETAILED DESCRIPTION

Figure 1:
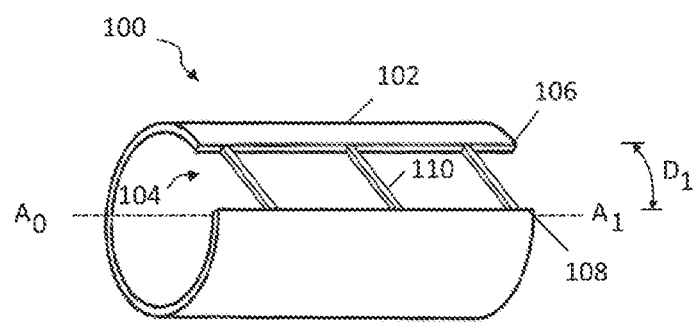
FIG. 1 is an elevational schematic view of a stent with bioresorbable struts having an expanded deployed diameter according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The drawings, which are not necessarily to scale, depict selected embodiments and are not intended to limit the scope of the disclosure. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner. As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

Unless defined otherwise, all technical and scientific terms used herein have the same meaning as commonly understood by one skilled in the art to which the disclosure pertains.

Finally, as used in this specification and the appended claims, the singular forms "a, "an" and "the" include plural referents unless the content clearly dictates otherwise.

Venous insufficiency generally involves the failure of valves in the vasculature to prevent retrograde flow of blood that would otherwise be returned to the heart. Typically, this condition is manifest in the extremities of a patient, such as the arms or legs. When the veins become over expanded, the valves that operate to counteract gravity as the blood returns to the heart no longer function adequately. Common symptoms of this disease are varicose veins and discomfort. A conventional treatment includes ablating the length of the vein, effectively closing it. In response, blood flow is rerouted to other veins under the assumption that they may not be subject to the same over expansion and correspondingly still have functioning valves. Accordingly, it would be desirable to develop a different treatment modality that does not involve this significant decrease in vascular capacity.

Since the failure of the valve or valves that causes this condition to develop results from over expansion of the veins, partial or complete restoration of function may be achieved by returning the vein to a diameter as close as possible to the original. As noted above, a stent is an implantable medical device that functions as a scaffold to reinforce the sections of the blood vessel in which it is deployed. Following implantation, a stent may be integrated into the vessel wall as the inner lining cells of the vessel wall grow over the framework of the stent in a process known as endothelialization. Effectively, the stent becomes pall of the vessel wall. Accordingly, the techniques of this disclosure involve the use a stent that is deployed within the vasculature in an expanded deployed diameter that is matched to the over expanded diameter of the vein suffering from venous insufficiency.

As a representative example only and without limitation, the diameter of the stent in the expanded deployed configuration may be in the range of approximately 15-25 mm, such as approximately 19 mm in one embodiment. Following deployment, the stent is endothelialized and integrated into the vessel wall. Portions of the stent are formed from a bioresorbable material that degrades upon exposure to biological tissue or fluid over a time period greater than endothelialization. Once the bioresorbable portions have degraded, the resiliency of the stent causes it to contract to a reduced deployed diameter that may be selected to match the desired diameter of the vessel so that valvular function may be at least partially restored. Again, as a representative example only, the diameter of the stent in the reduced deployed configuration is less than the expanded deployed diameter and may be in the range of approximately 5-15 mm, such as approximately 10 mm in the noted embodiment.

To help clarify the techniques of this disclosure, FIG. 1 is a schematic representation of a tubular stent 100, having a longitudinal axis $A_0$-$A_1$. In this depiction, a non-bioresorbable framework is represented as a partial cylindrical surface 102. Although shown as a continuous surface in the interests of clarity, one skilled in the art will appreciate that any suitable configuration of structural elements may be employed to form a lattice-like structure, including without limitation the helical winding and hoop-based designs described in further detail below. Further, the framework configuration may be designed to promote endothelialization or the surface of the framework may be treated to promote endothelialization, such as by using proliferative agents as noted below. As used herein, the term "non-bioresorbable" is intended to cover that class of biocompatible material used as biological implants that shows little or no degradation over time (e.g., at least 12 months) by actions of the host body when such material is implanted in the a biological vessel of the host body.

Cylindrical surface 102 is interrupted by a longitudinal zone 104 that extends from a proximal end of the stent to the distal end. Longitudinal zone 104 is defined by opposing longitudinal edges 106 and 108. A plurality of bioresorbable struts 110 are secured to the framework at opposing longitudinal edges 106 and 108. In this schematic depiction, stent 100 is shown in an expanded deployed diameter configuration that may be characterized in part by a distance $D_1$ between longitudinal edges 106 and 108 as shown. Typically, in one operational state stent 100 assumes the expanded deployed diameter configuration by being mechanically deformed into the increased diameter once positioned at a desired location within the patient's vasculature. For example, the stent may be delivered by a balloon catheter such that inflation of the balloon expands the stent into its expanded deployed diameter. As discussed above, stent 100 may be designed to have an expanded deployed diameter that matches the over expanded diameter of the vessel in which it is deployed so that it is brought into apposition with the vessel walls during deployment.

Bioresorbable struts 110 may be formed from a degradable material that is sufficiently ductile to allow deformation into a configuration that maintains longitudinal edges 106 and 108 at the $D_1$ distance. Notably, bioresorbable struts 110 also have sufficient strength in this deformed configuration to resist a contracting force that is imparted by the resiliency of the framework that forms cylindrical surface 102. For example, the framework may be formed from a shape memory alloy (e.g., Nitinol), with a remembered shape that corresponds to a reduced deployed diameter that may be characterized in part by a smaller distance between longitudinal edges 106 and 108. The material of bioresorbable struts 110 may be selected to resist degradation for a sufficient period of time to allow endothelialization of stent 100. Although as being substantially straight, bioresorbable struts 110 may have other configurations, such as "V"-shaped, "W"-shaped, "S"-shaped or others. Deformation of this configuration may facilitate maintaining the D1 distance between longitudinal edges 106 and 108 when stent 100 assumes the expanded deployed diameter.

Figure 2:
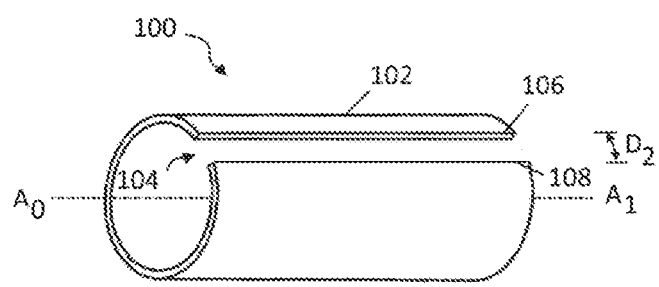
FIG. 2 is an elevational schematic view of a stent with bioresorbable struts having a reduced deployed diameter according to one embodiment.

Once bioresorbable struts 110 have degraded (after endothelialization), the resiliency of the framework of cylindrical surface 102 contracts stent 100 to another operational state having the configuration shown schematically in FIG. 2. It is noted that the non-bioresorbable framework 102 has an intrinsic characteristic or property that, tends to contract itself towards a more compact framework (e.g., a smaller diameter of FIG. 2) in the absence of any structural members opposing such intrinsic property of the non-bioresorbable framework 102 (e.g., members 110 in FIG. 1). This intrinsic property imparts sufficient resiliency to cause the non-bioresorbable framework 102 or stent to contract to the reduced deployed diameter when the plurality of bioresorbable struts 110 degrade or dissolves in the host body over time. To achieve this intrinsic characteristic of the non-bioresorbable framework to return to a compacted state, a shape memory alloy can be processed so that its solid-state phase transformation temperature (either austenite start temperature (As) or austenite final temperature (Af)) is set to be much higher (e.g., 60 to 120 degrees Celsius) than a host body temperature (typically 37-40 degrees Celsius) so that the non-bioresorbable framework does not self-expand by reversion of its structure to the austenite phase when the exemplary framework is placed in the host's body vessel due to the framework remaining in the martensite phase. This is in stark contrast to the known non-bioresorbable shape memory material that utilizes a material composition with an Af temperature at or near body temperature. The known shape memory material is designed with the Af temperature near body temperature to induce the known shape memory material to transform to a larger expanded diameter as the material of the known framework changes from its martensite phase to austenite phase. In other words, the exemplary non-bioresorbable frameworks described herein is intended to be self-contracting as opposed to being self-expanding for the known framework in the host body.

Without bioresorbable struts 110 holding longitudinal edges 106 and 108 apart, the distance between them contracts to a $D_2$ distance as indicated. Since stent 100 has been endothelialized and integrated into the vessel wall, contraction of stent 100 results in a corresponding contraction of the vessel diameter. The $D_2$ distance is less than the $D_1$ distance and corresponds to an overall reduced deployed diameter of stent 100 that may be designed to match a vessel diameter expected to at least partially restore function to the valves and ameliorate the venous insufficiency.

During delivery, stent 100 may assume a compressed diameter to facilitate introduction into and advancement through the patient's vasculature. For example, stent 100 may be crimped onto the balloon of a delivery catheter as known in the art. In the compressed diameter configuration, the framework of cylindrical surface 102 may be compressed and the distance between longitudinal edges 106 and 108 may be less than the $D_2$ distance.

Figure 3:
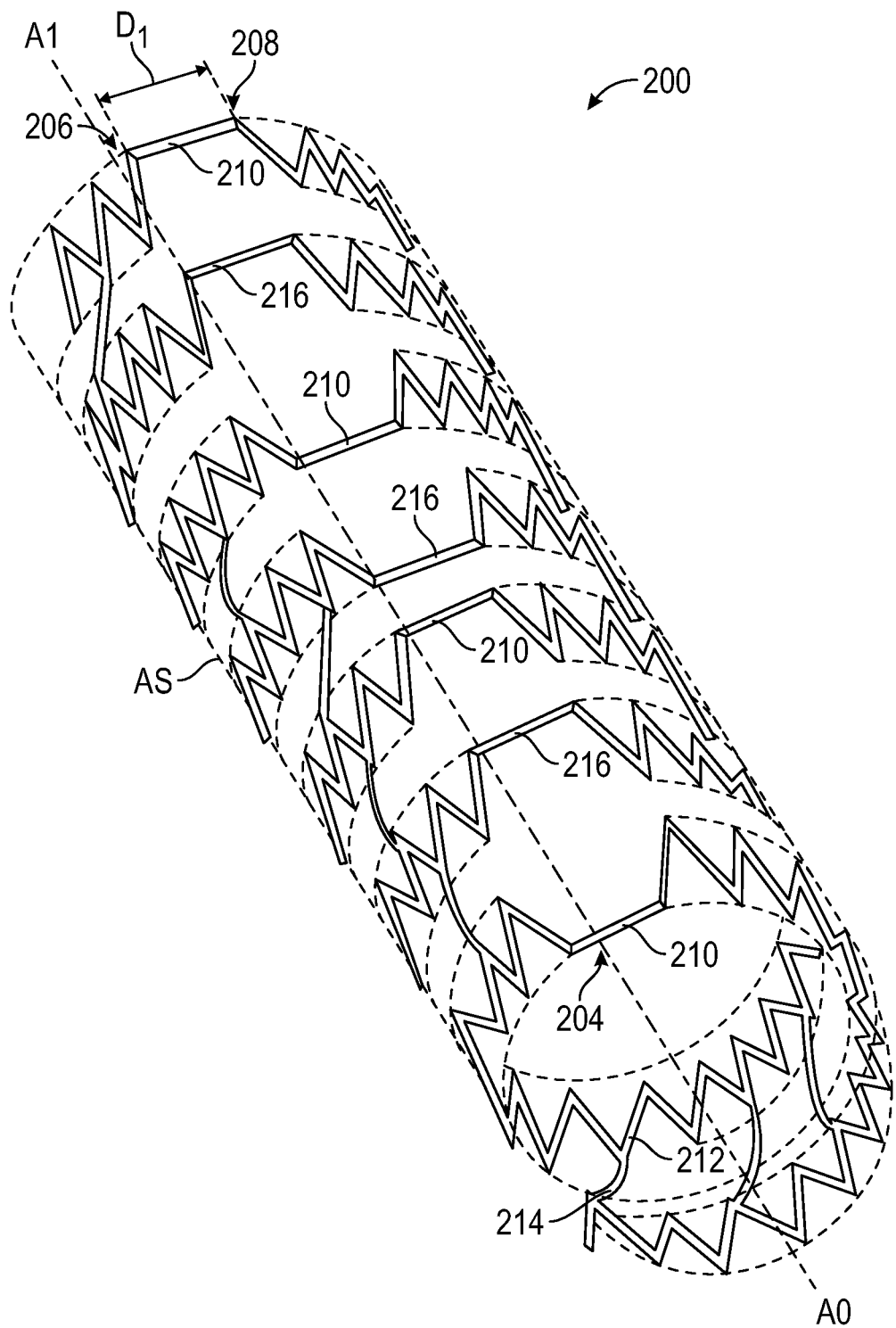
FIG. 3 is an elevational schematic view of a helical stent with bioresorbable struts having an expanded deployed diameter according to one embodiment.

As noted, cylindrical surface 102 may be a framework having any suitable design, including those used in conventional stent designs. For example, FIG. 3 illustrates an embodiment in which stent 200 employs a helical configuration. As with stent 100, stent 200 defines a generally cylindrical structure about a longitudinal axis $A_0$-$A_1$. Repeating zig-zag struts are formed into strings that follow a helical path to define the cylindrical shape of the stent, except in longitudinal zone 204 that extends from the proximal end to the distal end and is bounded by opposing longitudinal edges 206 and 208. A plurality of bioresorbable struts 210 maintain a distance $D_1$ between the longitudinal edges when stent 200 is in an expanded deployed configuration.

Zig-zag struts 212 generally comprise a repeating pattern of two struts connected by an apex, such that a plurality of strut pairs may be coupled and located on the helical path that circumscribes the axis $A_0$-$A_1$. Although the strut pairs shown are generally identical, each of the strut pairs can be of a different configuration. In circumscribing and translating along the axis, the helical path 10 follows a portion of a complete circle, except in the longitudinal zone 204, while at the same time translating along the axis $A_0$-$A_1$. As such, a plurality of arcuate sections "AS" defined by the successive pairing of strut pairs circumscribes the axis $A_0$-$A_1$ from a terminal first end to a terminal second end of the helical path to thereby define a partial cylindrical shape. A plurality of connector members 214 may extend in a generally longitudinal direction and be secured between helical windings by connecting adjacent arcuate sections. Further, although the arcuate sections are shown as being formed by alternating strut pairs, similar designs may employ struts that are disposed in an undulating, sinusoidal or wave-like pattern.

To aid the viewer in visualization of the helical path about the axis $A_0$-$A_1$ as defined by the zig-zag struts 212, the helical path is illustrated using dashed lines generally circumscribing about the axis $A_0$-$A_1$, having a first end $A_0$ and a second end $A_1$. To further aid visualization, stent 200 is illustrated with only the foreground structure, with the background structure such as struts that continue the helical path not displayed or only symbolically illustrated. It is noted that where the application of a covered stent is desired, the helical path is also a representation of another embodiment where the struts 212 are covered (partially or wholly) by a suitable material (e.g., ePTFE, Dacron, Nylon, fibrin, to name a few).

Figure 4:
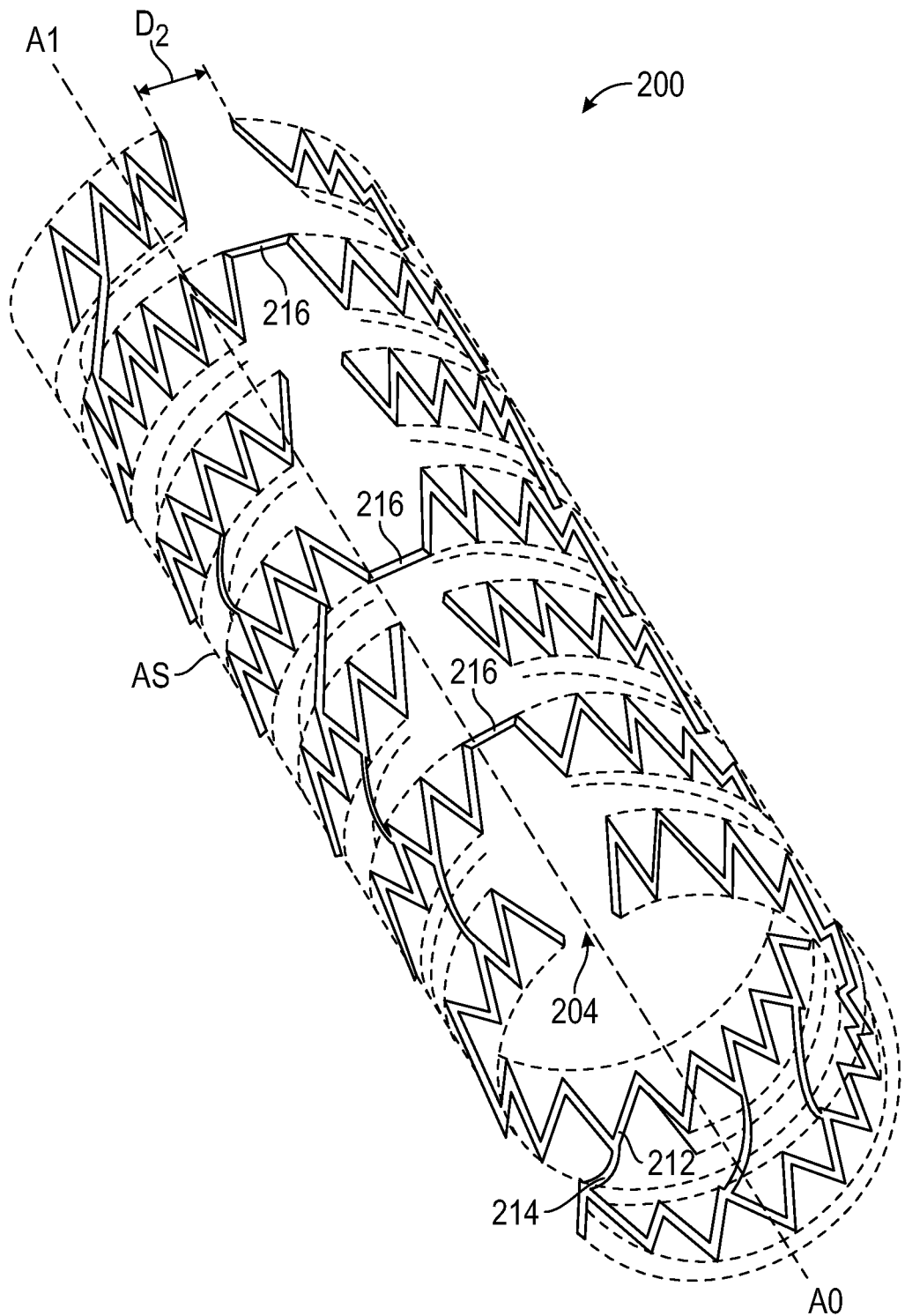
FIG. 4 is an elevational schematic view of a helical stem with bioresorbable struts having a reduced deployed diameter according to one embodiment.

Bioresorbable struts 210 may extend across longitudinal zone 204 to maintain distance $D_1$ as described above. As desired, each bioresorbable strut may extend between along the same helical winding to complete the helical path or may extend across longitudinal zone 204 to connect adjacent helical windings. In the embodiment shown, one or more additional non-bioresorbable struts 216 may also extend across longitudinal zone 204. When employed, non-bioresorbable struts 216 may help reinforce the remembered shape of stent 200 in the reduced deployed diameter in order to facilitate contraction of stent 200 when bioresorbable struts 210 degrade as shown in FIG. 4. As further shown in FIG. 4, non-bioresorbable struts 216 may also increase the structural integrity of stent 200 when bioresorbable struts 210 have degraded. Again, without the force imparted by the deformed bioresorbable struts 210, stent 200 contracts to its reduced deployed diameter that may be characterized in part by longitudinal edges 206 and 208 being separated by a distance $D_2$, less than $D_1$.

Although this and other embodiments of the disclosure have been described in the context of a single longitudinal zone, two or more longitudinal zones may be employed, each of which extend from the proximal end to the distal end. As described above, the width of the longitudinal zone is maintained by bioresorbable struts when the stent assumes its expanded deployed configuration, which is then reduced when the struts degrade and the stent contracts. When two or more longitudinal zones are employed, non-bioresorbable struts extending across the zones may be used to maintain the structural integrity of the stent following degradation of the bioresorbable stents.

Figure 5:
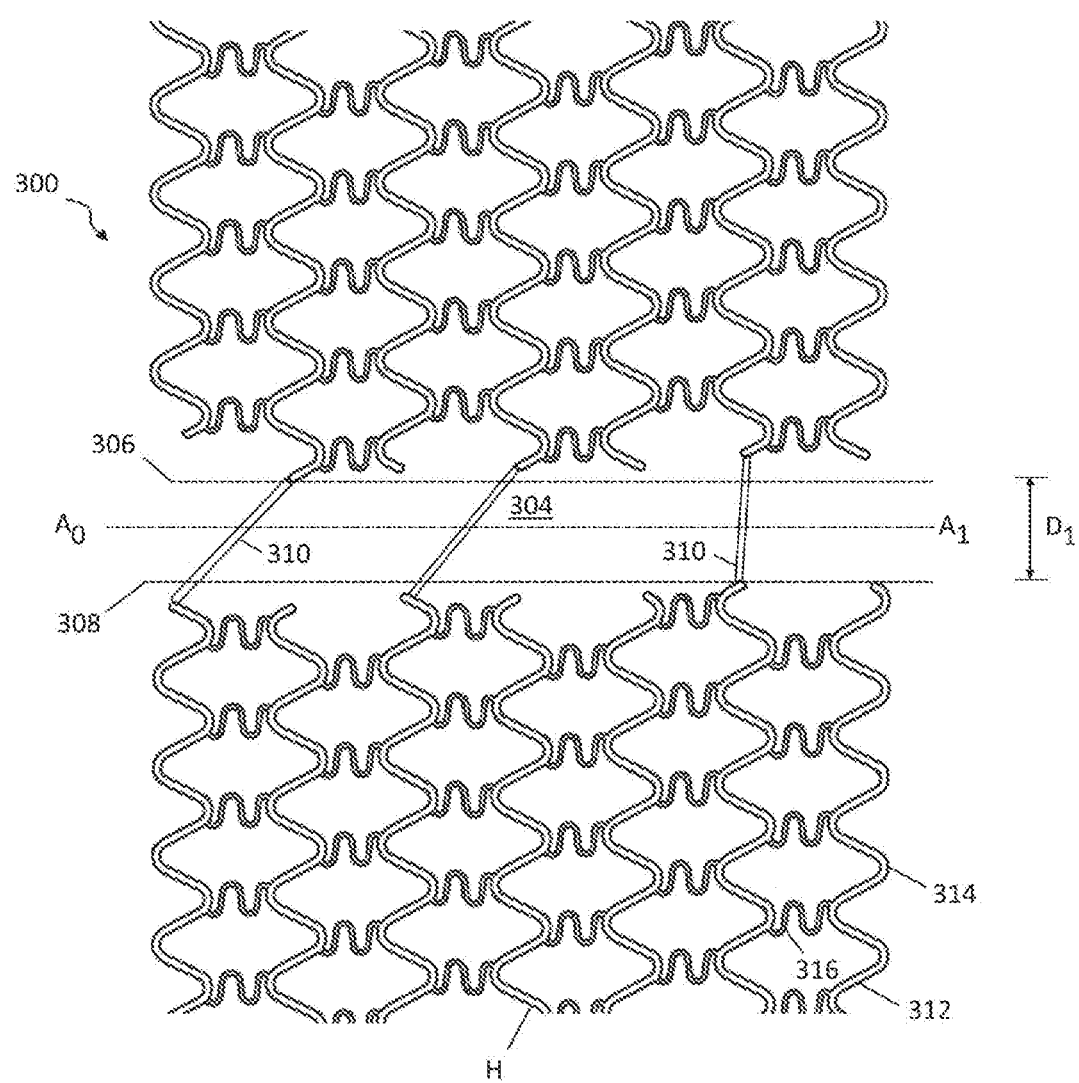
FIG. 5 is a top plan view of a hoop stent with bioresorbable struts cut along a longitudinal line and flattened according to one embodiment.

Another suitable design is exemplified by the hoop-based configuration of stent 300 as shown in FIG. 5, which is shown as being cut longitudinally and laid out flat in a 2-dimensional configuration. Again, stent 300 may define a generally cylindrical structure about a longitudinal axis $A_0$-$A_1$. A plurality of hoops are stacked longitudinally to define the cylindrical shape of the stent, except in longitudinal zone 304 that extends from the proximal end to the distal end and is bounded by opposing longitudinal edges 306 and 308. A plurality of bioresorbable struts 310 maintain a distance $D_1$ between the longitudinal edges when stent 300 is in an expanded deployed configuration.

Stent 300 structure comprises a plurality of adjacent hoops H extending between the proximal and distal ends of the stent along the longitudinal axis $A_0$-$A_1$. Each hoop is formed by a plurality of generally longitudinally arranged strut members 312 and a plurality of loop members 314 connecting adjacent struts. Adjacent struts 312 are connected at opposite ends in a substantially S or Z shaped pattern so as to form a plurality of cells. However, one of ordinary skill in the art would recognize that the pattern shaped by the struts is not a limiting factor in this invention, and other shaped patterns may be used. Adjacent hoops H are secured together by one or more connector members 316.

One suitable bioresorbable material for the bioresorbable struts of this disclosure, such as 110, 210 or 310, is one or more of a metal alloy shown and described in U.S. Pat. No. 6,287,332 or the metal alloy shown and described in U.S. Patent Application Publication No. 2002/0004060, which are incorporated by reference in their entirety. Preferably, the metallic bioresorbable material is selected from a first group consisting essentially of: magnesium, titanium, zirconium, niobium, tantalum, zinc, silicon, and combinations thereof. Also provided are mixtures and alloys of metallic bioresorbable materials, including those selected from the first group. Various alloys of the materials in the first group can also be used as a metallic bioresorbable material, such as a zinc-titanium alloy, for example, as described in U.S. Pat. No. 6,287,332 to Bolz et al. The physical properties of the alloy can be controlled by selecting the metallic bioresorbable material, or forming alloys of two or more metallic bioresorbable materials. For example, the percentage by weight of titanium can be in the range of about 0.1% to about 1%, which can reduce the brittle quality of crystalline zinc. Without being bound to theory, it is believed that the addition of titanium leads to the formation of a $Zn_{15}Ti$ phase. In another embodiment, gold can be added to the zinc-titanium alloy at a percentage by weight of about 0.1% to about 2%, which is believed to result in a further reduction of the grain size when the material cures and further improving the tensile strength of the material.

In some embodiments, the metallic bioresorbable material can be an alloy of materials from the first group and a material selected from a second group consisting essentially of: lithium, sodium, potassium, calcium, iron, manganese, and combinations thereof. The metallic bioresorbable material from the first group can form a protective oxide or passivation coating upon exposure to blood or interstitial fluid. The material from the second group is preferably soluble in blood or interstitial fluid to promote the dissolution of the oxide coating. Also provided are mixtures and alloys of metallic bioresorbable materials, including those selected from the second group and combinations of materials from the first group and the second group.

Briefly, the combination of metal materials can be a metal alloy, the selection of the alloy constituents serving to attain the prerequisite of biocompatible decomposition. Consequently, the metal alloy may consist of a combination of material that will decompose in the body comparatively rapidly while forming harmless constituents. Such alloy may include a component A which covers itself with a protective oxide coating. This component A is selected from one or several metals of the group of magnesium, titanium, zirconium, niobium, tantalum, zinc, silicon, or combinations thereof. For uniform dissolution of the protective oxide coating to be attained, a component B is added to the alloy, possessing sufficient solubility in blood or interstitial fluid, such as lithium sodium, potassium, calcium, iron or manganese. The corrosion rate is adjusted by way of the composition so that gases, such as hydrogen, which evolves during the corrosion of lithium, sodium, potassium, magnesium, calcium or zinc dissolve physically and essentially not forming any macroscopic gas bubbles. Other alloys can be utilized such as, for example, an alloy of lithium and magnesium in the ratio of about 60:40; a sodium-magnesium alloy; zinc-titanium alloy—the percentage by weight of which is in the range of about 0.1% to about 1% with gold being optionally added at a percentage by weight of about 0.1% to about 2%. Further details relating to these metallic bioresorbable materials are described in U.S. Pat. No. 6,287,332 to Bolz et al., which is incorporated herein by reference in its entirety.

Other materials for either the stent framework or the connectors can include biodegradable polymers such as polylactic acid (i.e., PLA), polyglycolic acid (i.e., PGA), polydioxanone (i.e., PDS), polyhydroxybutyrate (i.e., PHB), polyhydroxyvalerate (i.e., PHV), and copolymers or a combination of PUB and PHV (available commercially as Biopol®), polycaprolactone (available as Capronor®), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanoacrylates, or polyphosphazenes. As used herein, the term "bioresorbable" includes a suitable biocompatible material, mixture of materials or partial components of materials being degraded into other generally non-toxic materials by an agent present in biological tissue (i.e., being bio-degradable via a suitable mechanism, such as, for example, hydrolysis) or being removed by cellular activity bioresorption, bioabsorption, or bioresorbable), by bulk or surface degradation (i.e., bioerosion such as, for example, by utilizing a water insoluble polymer that is soluble in water upon contact with biological tissue or fluid), or a combination of one or more of the biodegradable, bioerodable, or bioresorbable material noted above.

In order to control the rate of degradation of the bioresorbable struts, the alloys or polymers may be adjusted as desired so that the bioresorbable struts remain intact for a period of time that allows the stent to be endothelialized, such as approximately 30 days. Other characteristics of the bioresorbable struts may also be adjusted to affect the degradation rate, such as by changing their relative size or by selecting different cross sectional profiles. In another aspect, the bioresorbable struts may be coated to delay degradation as desired. Accordingly, one technique of controlling the period of time after delivery that the arcuate sections or connector remain covered, and therefore not subject to resorption or degradation, can be provided by using a suitable material that changes chemical structure upon exposure to a particular activating wavelength of radiation (e.g., UV or visible light).

In one embodiment, the bioresorbable struts may be provided with a water repellant coating that prevents body fluids from degrading the resorbable material. Once exposed to the activating wavelength of radiation, the water repellant coating dissolves or becomes porous so that hydrolytic or enzymatic degradation of the underlying resorbable material can begin. In another example, exposure to a specific wavelength of light causes the light-activated material to change structure to thereby allow separation between the cover material and the underlying resorbable material. In an example, the activating radiation can be UV light, visible light or near infrared laser light at a suitable wavelength (e.g., 800 nanometers) at which tissues are substantially transparent. In a particular embodiment, the coating material may be polyethylene with a melting point of about 60 degrees Celsius mixed with biocompatible dyes that absorb radiation in the 800 nm range. Such dye can be Indocyanine green, which is a dye that absorbs radiation around 800 nm and is biocompatible, and will absorb the light energy and thereby raise the temperature in the polymer to about 60 degrees Celsius or higher. Upon attainment of the melting point temperature, the polymer structurally weakens thereby allowing the coating to lose integrity (i.e., crack, peal or otherwise become porous or at least a portion of the surface) thereby allowing biological fluid to come into contact with the underlying resorbable material and initiate the resorption process.

In a further aspect, one or more therapeutic agents may be incorporated into a coating applied to the stents of this disclosure or deposited into reservoirs that may be configured as recesses or through holes as known in the art. Polymeric matrices of either the coating or reservoir filling may be used to control elution of the agent(s). For example, a proliferative agent may be employed to facilitate or expedite endothelialization of the stent.

Non-genetic therapeutic agents include anti-thrombogenic agents such as heparin, heparin derivatives, urokinase, and PPack (dextrophenylalanine proline arginine chloromethylketone); antiproliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants, an ROD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor alpha and beta, platelet-derived endothelial growth factor, platelet-derived growth factor, tumor necrosis factor alpha, hepatocyte growth factor and insulin like growth factor, cell cycle inhibitors including CD inhibitors, thymidine kinase ("TK") and other agents useful for interfering with cell proliferation the family of bone morphogenic proteins ("BMPs"), BMP-2, BMP-3, BMP-4, BMP-5, BMP-6 (Vgr-1), BMP-7 (OP-I), BMP-8, BMP-9, BMP-IO, BMP-I, BMP-12, BMP-13, BMP-14, BMP-15, and BMP-16. Desirable BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or in addition, molecules capable of inducing an upstream or downstream effect of a BMP can be provided. Such molecules include any of the "hedgehog" proteins, or the DNA encoding them.

Cells can be of human origin (autologous or allogeneic) or from an animal source (xenogeneic), genetically engineered if desired to deliver proteins of interest at the deployment site. The cells may be provided in a delivery media. The delivery media may be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL® fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

The preferred stents may also be used as the framework for a vascular graft. Suitable coverings include nylon, collagen, PTFE and expanded PTFE, polyethylene terephthalate and KEVLAR®, ultra-high molecular weight polyethylene, or any of the materials disclosed in U.S. Pat. Nos. 5,824,046 and 5,755,770, which are incorporated by reference herein. More generally, any known graft material may be used including synthetic polymers such as polyethylene, polypropylene, polyurethane, polyglycolic acid, polyesters, polyamides, their mixtures, blends and copolymers.

Although the various embodiments have been described in relation to a framework that define essentially a portion of a tube using wire like members, other variations are within the scope of the invention. For example, other embodiments of the framework may define different cylindrical sections with different outer diameter; the framework may define a cylindrical section coupled to a conic section; the framework may define a single cone; the wire like members may be in cross-sections other than circular such as, for example, rectangular, square, or polygonal.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A stent comprising:
   a non-bioresorbable framework extending along a longitudinal axis having an at least partially cylindrical shape with proximal and distal ends;
   a longitudinal zone of the stent extending from the proximal end of the framework to the distal end, the longitudinal zone being defined by opposing longitudinal edges; and
   a plurality of bioresorbable struts, each bioresorbable strut being secured to the opposing longitudinal edges of the longitudinal zone to maintain the stent in one operational state having an expanded deployed diameter with the plurality of bioresorbable struts holding the opposing longitudinal edges a first distance apart such that upon degradation of the plurality of bioresorbable struts, the stent will contract to another operational state having a reduced deployed diameter so that the opposing longitudinal edges are a second distance apart that is less than the first distance, the non-bioresorbable framework having sufficient resiliency to cause the stent to contract to the reduced deployed diameter when the plurality of bioresorbable struts degrade.

2. The stent of claim 1, wherein the non-bioresorbable framework is formed from a nickel titanium shape memory alloy.

3. The stent of claim 1, further comprising at least one non-bioresorbable strut that is secured to the opposing longitudinal edges of the longitudinal zone, wherein the non-bioresorbable framework and the at least one non-bioresorbable strut have sufficient resiliency to cause the stent to contract to the reduced deployed diameter when the plurality of bioresorbable struts degrade.

4. The stent of claim 3, wherein at least one of the non-bioresorbable framework and the at least one non-bioresorbable strut is formed from a nickel titanium shape memory alloy.

5. The stent of claim 4, wherein both the non-bioresorbable framework and the at least one non-bioresorbable strut are formed from a nickel titanium shape memory alloy.

6. The stent of claim 1, wherein the plurality of bioresorbable struts are formed from a metal alloy.

7. The stent of claim 1, wherein the plurality of bioresorbable struts are formed from a polymer.

8. The stent of claim 1, wherein the plurality of bioresorbable struts degrade over a time period greater than approximately 30 days and less than approximately 12 months.

9. The stent of claim 1, wherein the framework comprises a plurality of arcuate sections circumscribing a longitudinal axis from the proximal end to the distal end, the plurality of arcuate sections spaced apart along the longitudinal axis to form at least one continuous helical path about the longitudinal axis except within the longitudinal zone.

10. The stent of claim 9, wherein at least one bioresorbable strut connects adjacent arcuate sections to continue the helical path through the longitudinal zone.

11. The stent of claim 9, wherein at least one bioresorbable strut is secured to ends of different helical windings.

12. The stent of claim 1, wherein the framework comprises a plurality of hoops spaced apart along a longitudinal axis with adjacent hoops connected to each other by respective connector members, each hoop comprising a repeating pattern of generally longitudinally aligned strut members connected by loop members.

13. The stent of claim 12, wherein at least one bioresorbable strut is secured to ends of a same hoop to form a continuous hoop.

14. The stent of claim 12, wherein at least one bioresorbable strut is secured to ends of different hoops.

15. A method for treating a patient, comprising:
providing a stent having an at least partially cylindrical non-bioresorbable framework extending along a longitudinal axis with proximal and distal ends, wherein a longitudinal zone of the stent extends from the proximal end of the framework to the distal end and is defined by opposing longitudinal edges, and a plurality of bioresorbable struts, each bioresorbable strut being secured to the opposing longitudinal edges of the longitudinal zone to maintain the stent in one operational state having an expanded deployed diameter with the plurality of bioresorbable struts holding the opposing longitudinal edges a first distance apart such that upon degradation of the plurality of bioresorbable struts, the stent will contract to another operational state having a reduced deployed diameter so that the opposing longitudinal edges are a second distance apart that is less than the first distance, the non-bioresorbable framework having sufficient resiliency to cause the stent to contract to the reduced deployed diameter when the plurality of bioresorbable struts degrade;
positioning the stent within a vessel of the patient; and
expanding the stent to an operational state having an expanded deployed diameter, so that the plurality of bioresorbable struts hold the opposing longitudinal edges a first distance apart, wherein the framework is in apposition with a wall defining the vessel.

16. The method of claim 15, further comprising allowing the bioresorbable struts to degrade following endothelialization of the stent, wherein degradation of the bioresorbable struts causes the stent to contract to another operational state having a reduced deployed diameter so that the opposing longitudinal edges are a second distance apart that is less than the first distance.

\* \* \* \* \*